United States Patent [19]
Lösel et al.

[11] 3,987,031
[45] Oct. 19, 1976

[54] ACYL DERIVATIVES OF PROSCILLARIDIN A

[75] Inventors: Walter Lösel; Herbert Merz, both of Ingelheim am Rhein; Wolfgang Hoefke, Budenheim; Werner Traunecker, Munster-Sarmsheim, all of Germany

[73] Assignee: Boehringer Ingelheim GmbH, Ingelheim am Rhein, Germany

[22] Filed: Dec. 5, 1973

[21] Appl. No.: 421,751

Related U.S. Application Data

[63] Continuation-in-part of Ser. No. 208,472, Dec. 15, 1971, abandoned.

[30] Foreign Application Priority Data

Dec. 23, 1970 Germany............................ 2063406

[52] U.S. Cl..................................... 536/6; 424/182
[51] Int. Cl.². ........................................... C07J 19/00
[58] Field of Search................................ 260/210.5

[56] References Cited
UNITED STATES PATENTS

| | | | |
|---|---|---|---|
| 3,472,836 | 10/1969 | Vogelsang et al. | 260/210.5 |
| 3,732,203 | 5/1973 | Stache et al. | 260/210.5 |
| 3,743,633 | 7/1973 | Goerlich et al. | 260/210.5 |
| 3,804,825 | 4/1974 | Losel et al. | 260/210.5 |

Primary Examiner—Johnnie R. Brown
Assistant Examiner—Cary Owens
Attorney, Agent, or Firm—Hammond & Littell

[57] ABSTRACT

Compounds of the formula

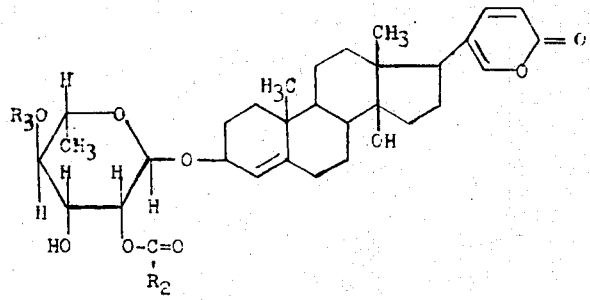

wherein $R_3$ is hydrogen, methyl, cyclopropylcarbonyl, benzoyl or thenoyl, and
when $R_3$ is hydrogen, $R_2$ is phenyl, phenethyl, phenylpropyl, chloro-propyl, chloro-phenyl, fluoro-phenyl, cycloalkyl of 3 to 8 carbon atoms or (cycloalkyl of 5 to 6 carbon atoms)-methyl, or
when $R_3$ is other than hydrogen, $R_2$ is methyl, ethyl, phenyl, cyclopropyl or chloropropyl; the compounds are useful as cardiotonics.

10 Claims, No Drawings

ACYL DERIVATIVES OF PROSCILLARIDIN A

This is a continuation-in-part of copending application Ser. No. 208,472, filed Dec. 15, 1971, now abandoned.

This invention relates to novel acyl derivatives of proscillaridin A, as well as to a method of preparing these compounds.

More particularly, the present invention relates to a novel class of acylated derivatives of proscillaridin A represented by the formula

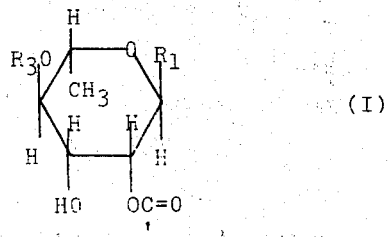
(I)

wherein $R_1$ is

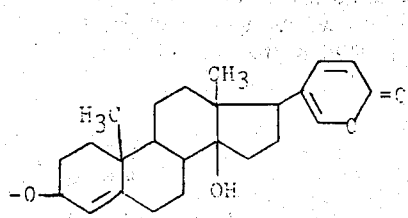

wherein $R_3$ is hydrogen, methyl, cyclopropylcarbonyl, benzoyl or thenoyl, and when $R_3$ is hydrogen, $R_2$ is phenyl, phenethyl, phenylpropyl, chloropropyl, chloro-phenyl, fluoro-phenyl, cycloalkyl of 3 to 8 carbon atoms or (cycloalkyl of 5 to 6 carbon atoms)-methyl, or when $R_3$ is other than hydrogen, $R_2$ is methyl, ethyl, phenyl, cyclopropyl or chloropropyl.

The compounds of the formula I are prepared by subjecting a glycoside of the formula

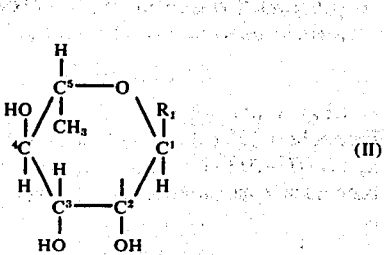
(II)

wherein $R_1$ has the meaning defined in formula I, to an ester exchange reaction with an ortho-ester of the formula

$R_2 - C(OR_4)_3$ (III)

wherein $R_2$ has the same meanings as in formula I and $R_4$ is lower alkyl, to form a cyclic ortho-ester of the formula

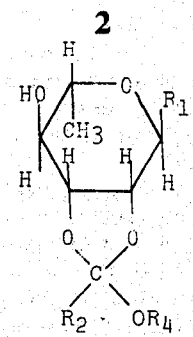
(IV)

wherein $R_1$, $R_2$ and $R_4$ have the meanings defined above, optionally esterifying or etherifying the hydroxyl group in the $C^4$-position with an alkylating or acylating agent of the formula

$R_3X$ (V)

wherein $R_3$ has the same meanings as in formula I except hydrogen and X is halogen or another anionically easily removable radical, and, after optionally isolating the intermediate product of the formula

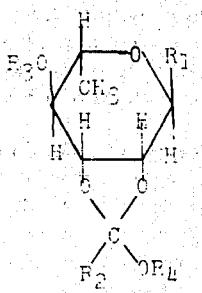
(IVa)

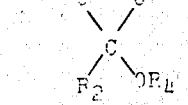

wherein $R_1$, $R_2$, $R_3$ and $R_4$ have the meanings defined above, subjecting the intermediate IVa to partial hydrolysis.

The ester exchange reaction for the preparation of the ortho-ester of the formula IV is carried out in the presence of an acid catalyst and, if desired, in the presence of an inert organic solvent, such as tetrahydrofuran, dioxane, chloroform or methylene chloride. Suitable acid catalysts are inorganic or strong organic acids, such as hydrohalic acids, sulfuric acid, p-toluenesulfonic acid, methane-sulfonic acid or trichloroacetic acid; Lewis acids, such as potassium bisulfate, zinc chloride, borontrifluorideetherate or copper sulfate; or acid ion-exchangers, such as Amberlite IR 120 or Dowex 50.

The ester exchange reaction may be performed at a temperature between 0° C and the reflux temperature of the reaction mixture, but preferably at about room temperature.

The subsequent partial hydrolysis of the intermediate cyclic ortho-ester of the formula IVa is carried out in the presence of an aqueous acid; if the intermediate ortho-ester has previously been isolated, it is dissolved again in an inert organic solvent, such as ethyl acetate, prior to being subjected to partial hydrolysis.

We have found that it is particularly advantageous to admix the reaction mixture resulting from the ester exchange reaction with the aqueous acid and to perform the partial hydrolysis in situ therein. Any desired aqueous acid solution having a pH of 4 or less may be used. The hydrolysis reaction proceeds in stereo-selective fashion, that is, as a rule, the hydrolysis product consists uniformly of the derivative with an esterified OH-group in the 2'-position to the exclusion of all other possible derivatives.

The acylation of the free hydroxyl group in the C⁴-position may be effected according to any conventional acylation process, provided the stability of the cyclic ortho-ester of the formula IVa permits it. For example, it may be effected with a reactive derivative of the desired acid, such as an acyl halide, an acid anhydride or a mixed anhydride of an acid and a carbonic acid monoester, at room temperature in the presence of an inert solvent and an acid-binding agent. Suitable acid-binding agents are inorganic or tertiary organic bases; the latter, such as pyridine, may simultaneously serve as the solvent medium if they are provided in sufficient excess. In order to accelerate the acylation, 4-dimethylamino-pyridine may be added as an acylation catalyst, and in that case the reaction may be carried out with or without the addition of triethylamine.

The alkylation of the free hydroxyl group in the C⁴-position is preferably carried out with an alkyl iodide in the presence of silver oxide in dimethylformamide as the solvent medium.

The starting compound of the formula II is proscillaridin A, which is a known compound and may, for example, be isolated pursuant to known methods from white squill [see A. Stoll et al, Helv. Chim. Acta 34, 1431 (1951)].

The following examples further illustrate the present invention and will enable others skilled in the art to understand it more completely. It should be understood, however, that the invention is not limited solely to the particular examples given below.

EXAMPLE 1

2'-Benzoyl-proscillaridin A 50 mgm of p-toluenesulfonic acid and 1 ml of ortho-benzoic acid triethyl ester were added to a solution of 1 gm of proscillaridin A in 20 ml of absolute tetrahydrofuran, and the mixture was stirred at room temperature until the reaction had gone to completion. In order to hydrolize the cyclic ortho-ester formed thereby, 2 ml of water and an additional 50 mgm of p-toluenesulfonic acid were added to the reaction mixture. After completion of the hydrolysis, the reaction solution was neutralized with triethylamine and evaporated in vacuo on a water bath at 50° C, and the residue was recrystallized from ethanol, yielding 1.015 gm of the compound of the formula

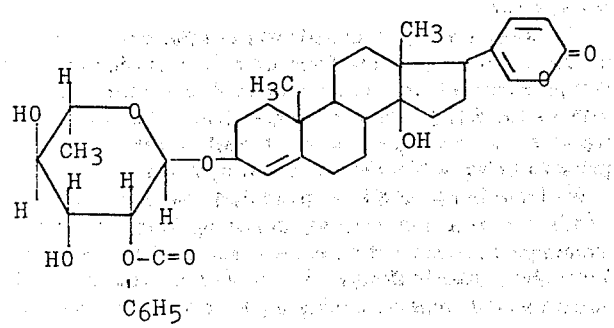

having a melting point of 236°–240° C.

EXAMPLE 2

Using a procedure analogous to that described in Example 1, 2'-(γ-chloro-butyryl)-proscillaridin A, m.p. 183°–184° C, of the formula

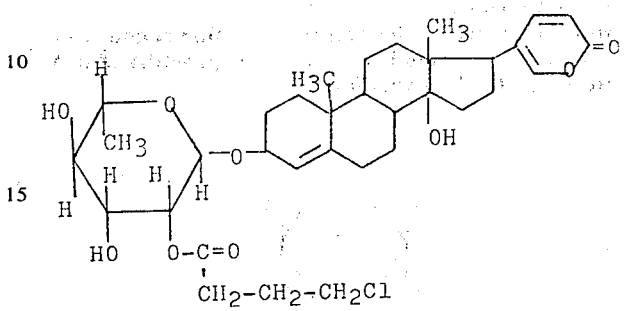

was prepared from ortho-γ-chlorobutyric acid trimethyl ester and proscillaridin A.

EXAMPLE 3

Using a procedure analogous to that described in Example 1, 2'-(cyclopropylcarbonyl)-proscillaridin A, m.p. 196°–210° C, of the formula

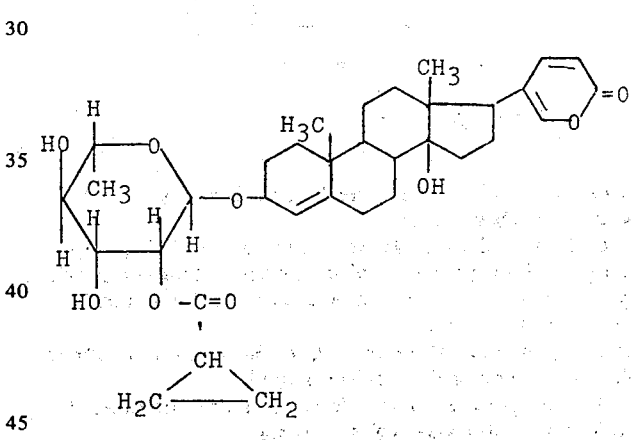

was prepared from ortho-cyclopropanecarboxylic acid trimethyl ester and proscillaridin A.

EXAMPLE 4

Using a procedure analogous to that described in Example 1, 2'-(cyclopentylcarbonyl)-proscillaridin A, m.p. 201°–203° C, was prepared from ortho-cyclopentanecarboxylic acid trimethyl ester and proscillaridin A.

EXAMPLE 5

Using a procedure analogous to that described in Example 1, 2'-(cyclohexylcarbonyl)-proscillaridin A, m.p. 218°–223° C, was prepared from ortho-cyclohexanecarboxylic acid trimethylester and proscillaridin A.

EXAMPLE 6

Using a procedure analogous to that described in Example 1, 2'-(cyclooctylcarbonyl)-proscillaridin A, an amorphous substance, was prepared from ortho-cyclooctanecarboxylic acid trimethyl ester and proscillaridin A.

EXAMPLE 7

Using a procedure analogous to that described in Example 1, 2'-(cyclopentylacetyl)-proscillaridin A, m.p. 159°–161° C, of the formula

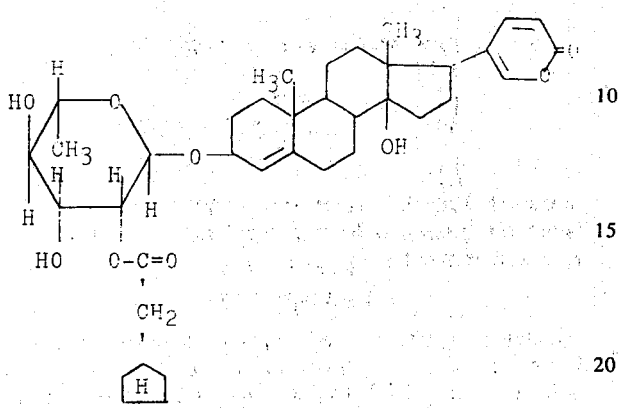

was prepared from ortho-cyclopentylacetic acid trimethyl ester and proscillaridin A.

EXAMPLE 8

Using a procedure analogous to that described in Example 1, 2'-(cyclohexylacetyl)-proscillaridin A, m.p. 187°–190° C, was prepared from ortho-cyclohexylacetic acid trimethyl ester and proscillaridin A.

EXAMPLE 9

Using a procedure analogous to that described in Example 1, 2'-(β-phenylpropionyl)-proscillaridin A, of the formula

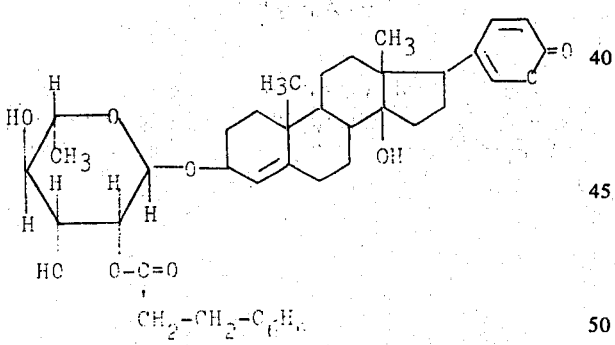

NMR: Taken up in dimethylsulfoxide
δ = 7.2 ppm; Singulett (5 protons)

δ = 2.77 ppm; Multiplett (2 protons)

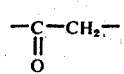

Standard: TMS δ = 10.00 ppm, (TMS = tetramethylsilane) was prepared from ortho-β-phenylpropionic acid trimethyl ester and proscillaridin A.

EXAMPLE 10

Using a procedure analogous to that described in Example 1, 2'-(γ-phenylbutyryl)-proscillaridin A, NMR: Taken up in CDCl₃ (deuterochloroform)
δ = 2.7 ppm; Singulett (5 protons)

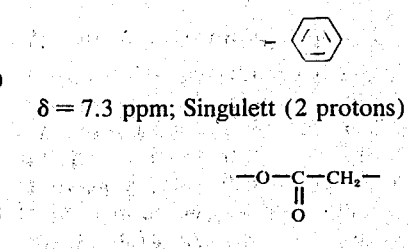

δ = 7.3 ppm; Singulett (2 protons)

$$-O-C-CH_2-$$
$$\phantom{-O-}\|\phantom{-CH_2}$$
$$\phantom{-O-}O\phantom{-CH_2}$$

Standard: TMS δ = 10.00 ppm (TMS = tetramethylsilane) was prepared from ortho-γ-phenylbutyric acid trimethyl ester and proscillaridin A.

EXAMPLE 11

Using a procedure analogous to that described in Example 1, 2'-(p-fluorobenzoyl)-proscillaridin A, m.p. 154°–160° C, of the formula

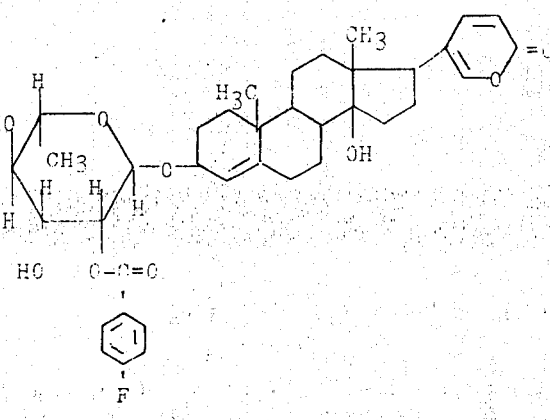

was prepared from ortho-p-fluorobenzoic acid trimethyl ester and proscillaridin A.

EXAMPLE 12

Using a procedure analogous to that described in Example 1, 2'-(p-chlorophenyl-acetyl)-proscillaridin A, m.p. 132°–142° C, of the formula

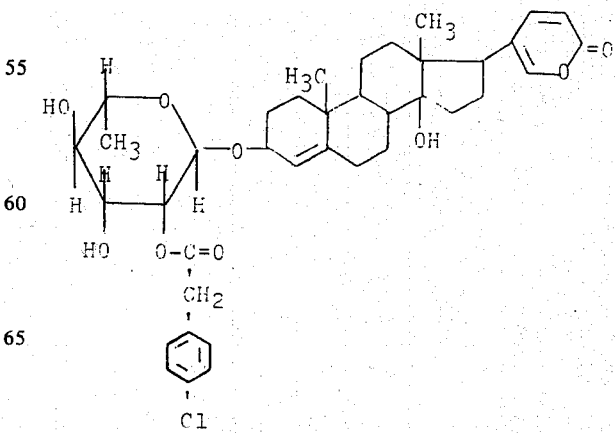

was prepared from ortho-p-chlorophenylacetic acid trimethyl ester and proscillaridin A.

EXAMPLE 13

2′-Propionyl-4′-cyclopropylcarbonyl-proscillaridin A 1 gm of proscillaridin A was reacted with orthopropionic acid triethyl ester in a manner analogous to that described in Example 1, and the reaction mixture was neutralized with triethylamine. The resulting solution was evaporated, the residue was dissolved in pyridine, and the resulting solution was reacted with 1 ml of cyclopropanecarboxylic acid chloride while stirring and cooling on an ice bath. Thereafter, the reaction mixture was again neutralized, the solvent was distilled off in vacuo, the residue was taken up in chloroform and shaken with 2 N hydrochloric acid, the organic phase was washed with water, dried over sodium sulfate and evaporated, and the residue was recrystallized from ethyl acetate/petroleum ether, yielding 79% of theory of the compound of the formula

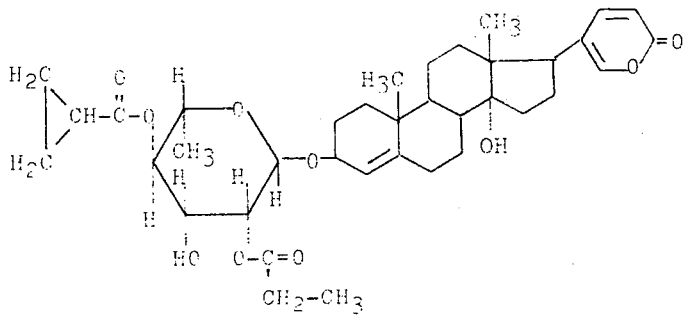

having a melting point of 190°–195° C.

EXAMPLE 14

Using a procedure analogous to that described in Example 13, 2′,4′-dibenzoyl-proscillaridin A of the formula

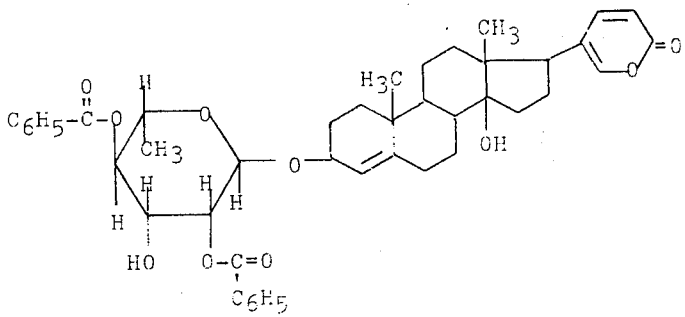

NMR: Taken up in CDCl$_3$ (deuterochloroform)
δ = 8.05 ppm; Multiplett (4 protons)

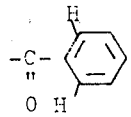

δ = 7.55 ppm; Multiplett (6 protons)

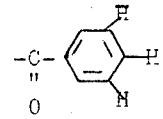

Standard: TMS δ - 10.00 ppm, (TMS = tetramethylsilane) was prepared from proscillaridin A, ortho-benzoic acid triethyl ester and benzoyl chloride.

EXAMPLE 15

Using a procedure analogous to that described in Example 13, 2′,4′-di-(cyclopropylcarbonyl)-proscillaridin A, m.p. 132°–134° C, was prepared from proscillaridin A orthocyclopropanecarboxylic acid trimethyl ester and cyclopropanecarboxylic acid chloride.

EXAMPLE 16

Using a procedure analogous to that described in Example 13, 2′-(γ-chlorobutyryl)-4′-cyclopropylcarbonylproscillaridin A, m.p. 105°–117° C, of the formula

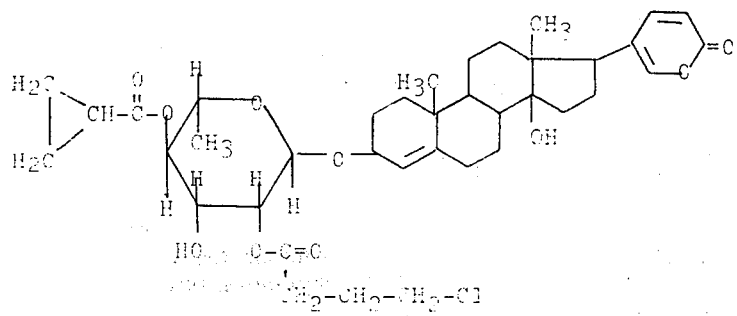

was prepared from proscillaridin A, ortho-γ-chlorobutyric acid trimethyl ester and cyclopropanecarboxylic acid chloride.

EXAMPLE 17

Using a procedure analogous to that described in Example 13, 2'-benzoyl-4'-(2-thenoyl)-proscillaridin A, m.p. 164°–170° C, of the formula

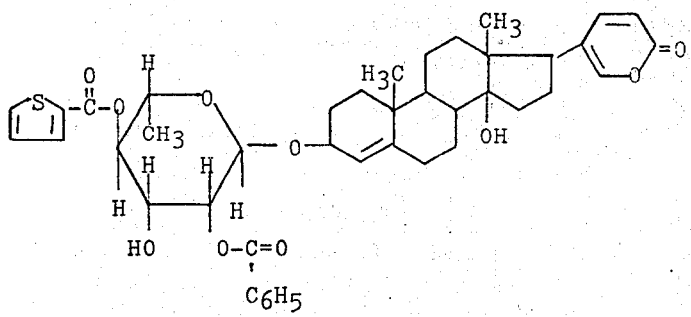

was prepared from proscillaridin A, ortho-benzoic acid trimethylester and 2-thenoic acid chloride.

EXAMPLE 18

2'-Acetyl-4'-methyl-proscillaridin A 1 gm of proscillaridin A was reacted with orthoacetic acid triethyl ester in a manner analogous to that described in Example 1. The resulting reaction mixture was neutralized with triethylamine, the solvent was distilled off in vacuo, the residue was dissolved in 30 ml of dimethylformamide, and the solution was stirred with 2 gm of silver oxide and 2 ml of methyl iodide for 20 hours at room temperature under exclusion of light. Thereafter, the solvent was evaporated in vacuo, and the residue was recrystallized from chloroform/ether, yielding 787 mgm (69.5 percent of theory) of the compound of the formula

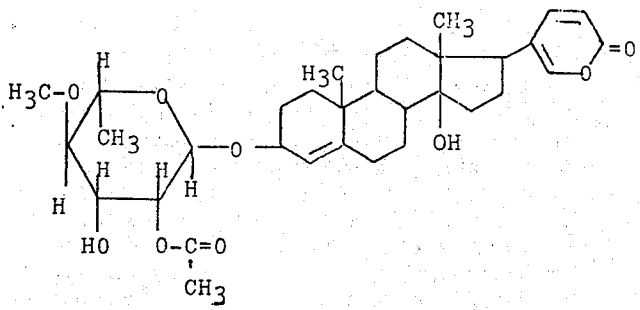

having a melting point of 140°–148° C.

EXAMPLE 19

Using a procedure analogous to that described in Example 18, 2'-propionyl-4'-methyl-proscillaridin A, m.p. 154°–156° C, was prepared from proscillaridin A, ortho-propionic acid trimethyl ester and methyl iodide/silver oxide.

EXAMPLE 20

Using a procedure analogous to that described in Example 18, 2'-cyclopentylcarbonyl-4'-methyl-proscillaridin A, m.p. 123°–134° C, was prepared from proscillaridin A, orthocyclopentanecarboxylic acid trimethyl ester and methyl iodide/silver oxide.

The compounds according to the present invention, that is, those embraced by formula I above, have useful pharmacodynamic properties. More particularly, the compounds of the instant invention exhibit cardiotonic and especially positive inotropic activities in the isolated ventricle of the guinea pig heart as well as in the heart-lung preparation, and are therefore useful for the treatment of cardiac insufficiency in warm-blooded animals. The cardiotonic activity of the compounds of the present invention is superior to and their toxicities significantly less than that of g-strophanthidin.

For pharmaceutical purposes the compounds according to the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective cardiotonic dosage unit of the compounds according to the present invention is from 0.00083 to 0.084 mgm/kg body weight, preferably from 0.002 to 0.034 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 21

Tablets

The tablet composition is compounded from the following ingredients:

| | | |
|---|---:|---|
| 2-(β-phenyl-propionyl)-proscillaridin A | 0.25 | parts |
| Lactose | 85.75 | parts |
| Potato starch | 30.0 | parts |
| Gelatin | 3.0 | parts |
| Magnesium stearate | 1.0 | parts |
| Total | 120.0 | parts |

PREPARATION:

The glycoside is intensively milled with ten times its weight of lactose, the milled mixture is admixed with the remaining amount of the lactose and the potato starch, the resulting mixture is moistened with an aqueous 10 percent solution of the gelatin, the moist mass is forced through a 1.5 mm-mesh screen, and the resulting granulate is dried at 40° C. The dry granulate is again passed through a 1 mm-mesh screen, admixed with the magnesium stearate, and the composition is compressed into 120 mgm-tablets in a conventional tablet making machine. Each tablet contains 0.25 mgm of the glycoside and is an oral dosage unit composition with effective cardiotonic action.

EXAMPLE 22

Coated pills

The pill core composition is compounded from the following ingredients:

| | | |
|---|---|---|
| 2'-(γ-chloro-butyryl)-proscillaridin A | 0.25 | parts |
| Lactose | 32.25 | parts |
| Corn starch | 15.00 | parts |
| Polyvinylpyrrolidone | 2.00 | parts |
| Magnesium stearate | 0.50 | parts |
| Total | 50.0 | parts |

PREPARATION:

The glycoside is intensively milled with ten times its weight of lactose, the milled mixture is admixed with the remainder of the lactose and the corn starch, the mixture is moistened with an aqueous 15 percent solution of the polyvinylpyrrolidone, the moist mass is forced through a 1 mm-mesh screen, and the resulting granulate is dried at 40° C and again passed through the screen. The dry granulate is admixed with the magnesium stearate, and the resulting composition is compressed into 50 mgm-pill cores which are subsequently coated in conventional manner with a thin shell consisting essentially of a mixture of sugar and talcum and finally polished with beeswax. Each coated pill contains 0.25 mgm of the glycoside and is an oral dosage unit composition with effective cardiotonic action.

EXAMPLE 23

Drop solution

The solution is compounded from the following ingredients:

| | | |
|---|---|---|
| 2'-(β-phenyl-propionyl)-proscillaridin A | 0.0125 | parts |
| Saccharin sodium | 0.3 | parts |
| Sorbic acid | 0.1 | parts |
| Ethanol | 30.0 | parts |
| Flavoring | 1.0 | parts |
| Distilled water q.s.ad | 100.0 | parts |

PREPARATION:

The glycoside and the flavoring are dissolved in the ethanol, and the sorbic acid and the saccharin sodium are dissolved in the distilled water. The two solutions are uniformly admixed with each other, and the mixed solution is filtered until free from suspended matter. 1 ml of the filtrate contains 0.125 mgm of the glycoside and is an oral dosage unit composition with effective cardiotonic action.

EXAMPLE 24

Hypodermic solution

The solution is compounded from the following ingredients:

| | | |
|---|---|---|
| 2'-Acetyl-4'-methyl-proscillaridin A | 0.25 | parts |
| Polyethyleneglycol 600 | 700.0 | parts |
| Tartaric acid | 150.0 | parts |
| Distilled water q.s.ad | 3000.0 | parts by vol. |

PREPARATION:

The tartaric acid, the polyethyleneglycol and the glycoside are successively dissolved in a sufficient amount of distilled water, and the resulting solution is diluted with distilled water to the indicated volume and then filtered until free from suspended matter. The filtrate is filled into white 3 ml-ampules in an atmosphere of nitrogen, which are then sterilized for 20 minutes at 120° C and sealed. Each ampule contains 0.25 mgm of the glycoside, and the contents thereof are an injectable dosage unit composition with effective cardiotonic action.

EXAMPLE 25

Suppositories

The suppository composition is compounded from the following ingredients:

| | | |
|---|---|---|
| 2'-cyclopentylcarbonyl-proscillaridin A | 0.25 | parts |
| Lactose | 4.75 | parts |
| Suppository base (e.g. cocoa butter) | 1695.0 | parts |
| Total | 1700.0 | parts |

PREPARATION:

The glycoside and the lactose are admixed, and the mixture is milled. The milled mixture is uniformly stirred with the aid of an immersion homogenizer into the suppository base, which had previously been melted and cooled to 40° C. The resulting composition is cooled to 37° C, and 1700 mgm-portions thereof are poured into cooled suppository molds and allowed to harden therein. Each suppository contains 0.25 mgm of the glycoside and is a rectal dosage unit composition with effective cardiotonic action.

Analogous results are obtained when any one of the other acylated glycosides embraced by formula I was substituted for the particular acylated glycoside in Examples 21 through 25. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. A compound of the formula

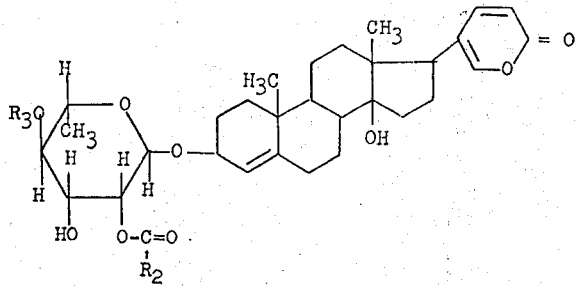

wherein $R_3$ is hydrogen, methyl, cyclopropylcarbonyl, benzoyl or thenoyl, and
when $R_3$ is hydrogen, $R_2$ is phenyl, phenethyl, phenyl-propyl, chloropropyl, chlorophenyl, fluoro-phenyl, cycloalkyl of 3 to 8 carbon atoms or (cycloalkyl of 5 to 6 carbon atoms)-methyl, or
when $R_3$ is other than hydrogen, $R_2$ is methyl, ethyl, phenyl, cyclopropyl or chloropropyl.

2. The compound of claim 1, which is 2'-(β-phenyl-propionyl)-proscillaridin A.
3. The compound of claim 1, which is 2'-(γ-chloro-butyryl)-proscillaridin A.
4. The compound of claim 1, which is 2'-(cyclopentyl-carbonyl)-proscillaridin A.
5. The compound of claim 1, which is 2'-acetyl-4'-methyl-proscillaridin A.
6. The compound of claim 1, which is 2'-cyclopropyl-carbonyl-proscillaridin A.
7. The compound of claim 1, which is 2'-(p-chlorophenyl-acetyl)-proscillaridin A.
8. The compound of claim 1, which is 2'-propionyl-4'-methyl-proscillaridin A.
9. The process for the preparation of a compound of the formula

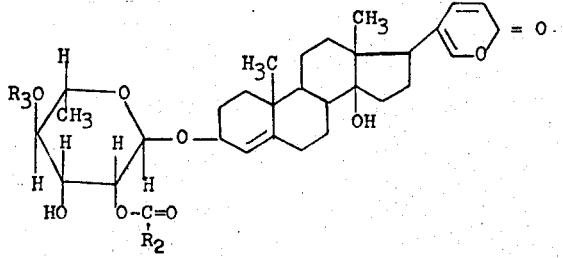

wherein $R_3$ is hydrogen, and
$R_2$ is phenyl, phenethyl, phenyl-propyl, chloropropyl, chloro-phenyl, fluoro-phenyl, cycloalkyl of 3 to 8 carbon atoms or (cycloalkyl of 5 to 6 carbon atoms)-methyl,
which consists essentially of subjecting proscillaridin A to an ester exchange reaction with an ortho-ester of the formula $R_2 - C(OR_4)_3$ wherein $R_2$ has the meanings defined above and $R_4$ is lower alkyl, to form an intermediate cyclic ortho-ester of the formula

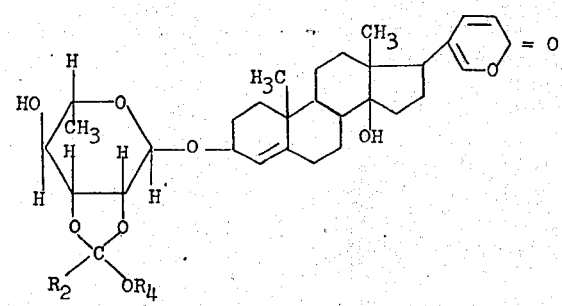

wherein $R_2$ and $R_4$ have the meanings defined above, and subjecting said intermediate to acid hydrolysis at a pH of no more than 4.

10. The process of claim 9, wherein $R_3$ is methyl, cyclopropylcarbonyl, benzoyl or thenoyl, and
$R_2$ is methyl, ethyl, phenyl, cyclopropyl or chloropropyl,
which comprises the step of reacting said intermediate cyclic ortho-ester with a compound of the formula $R_3X$ wherein $R_3$ has the meanings defined above, and X is chlorine, prior to said acid hydrolysis.

* * * * *